United States Patent [19]
Andrews

[11] 3,959,880
[45] June 1, 1976

[54] SPRING-STRESSED ORTHODONTIC BRACKET

[76] Inventor: Lawrence F. Andrews, 2025 Chatsworth Blvd., San Diego, Calif. 92107

[22] Filed: Aug. 14, 1974

[21] Appl. No.: 497,281

[52] U.S. Cl. .............................................. 32/14 A
[51] Int. Cl.² ......................................... A61C 7/00
[58] Field of Search .................................. 32/14 A

[56] References Cited
UNITED STATES PATENTS

| | | | |
|---|---|---|---|
| 1,976,115 | 10/1934 | Boyd et al............................ | 32/14 A |
| 2,379,011 | 6/1945 | Laskin................................. | 32/14 A |
| 2,381,128 | 8/1945 | Laskin................................. | 32/14 A |
| 3,780,437 | 12/1973 | Wildman.............................. | 32/14 A |

*Primary Examiner*—Robert Peshock

[57] ABSTRACT

A spring-stressed orthodontic bracket in which the bracket consists of two complementary jaw members which define an archwire groove when brought together in slidable relationship on a base member. A spring-biasing wire extends around or through the periphery forcing them together. Suitable limit pins are utilized in conjunction with a base member for limiting the movement of each of the complementary jaw members. The spring wire can also supply a rotational force against an archwire when installed.

6 Claims, 8 Drawing Figures

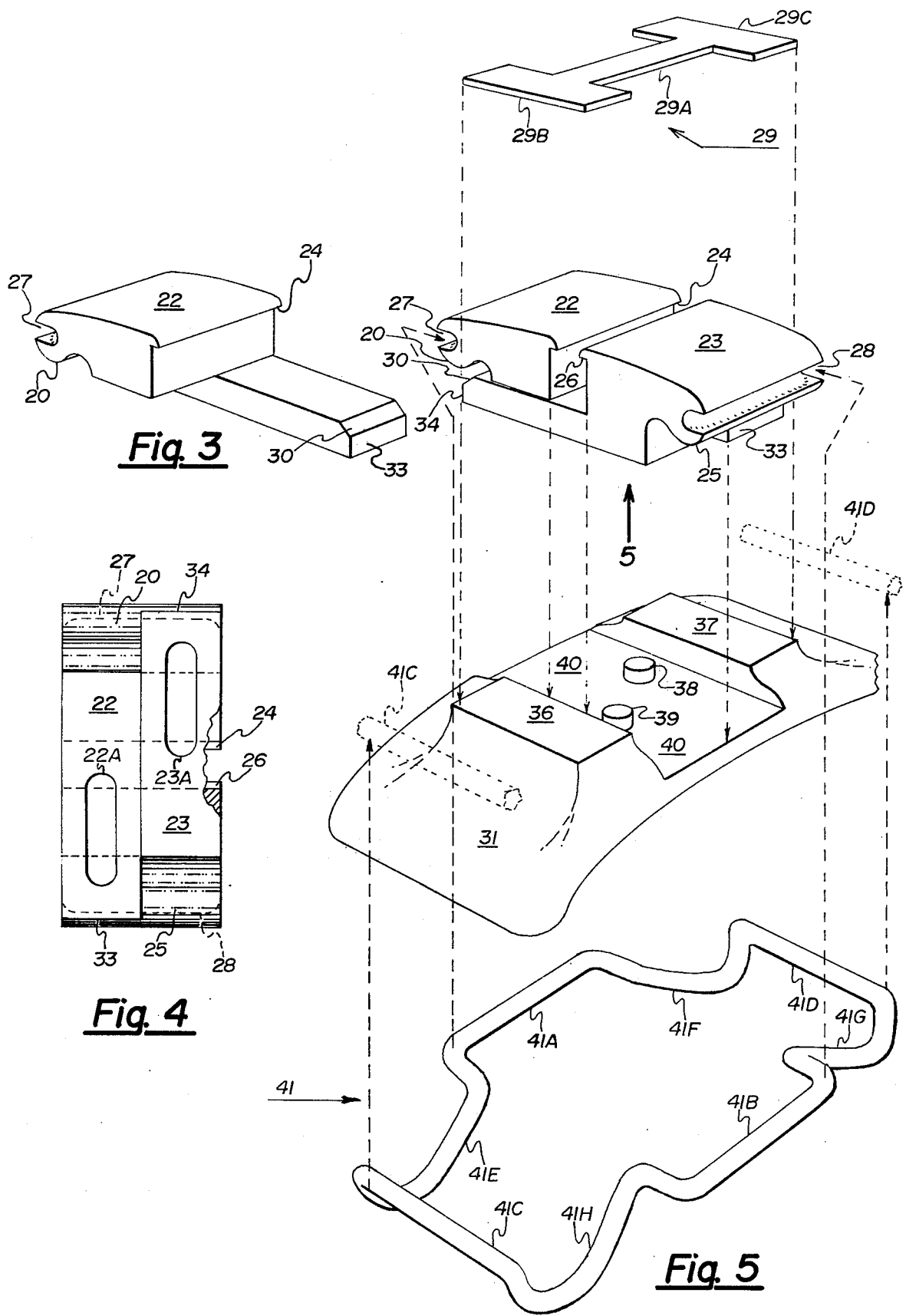

SPRING-STRESSED ORTHODONTIC BRACKET

PRIOR ART

The following patents were discovered in a preliminary patentability search:

| | |
|---|---|
| 2,908,974 | 3,414,976 |
| 3,052,027 | 3,599,331 |
| 3,164,900 | 3,691,635 |

BRIEF DESCRIPTION OF THE INVENTION

According to the invention, a spring-stressed orthodontic bracket is provided for the reception of an archwire in which the bracket defining the archwire groove consists of complementary jaw members. A base member is supplied with a groove therein for the reception of two sliding tongues, one from each single jaw of the complementary members so that the members defining the groove can move with respect to each other, in effect, widening the groove and narrowing within limits set by limit pins in the base member and a retainer plate. A tension spring is carried around the periphery of the complementary jaw members for applying a force to the jaw members which tends to force them together, i.e., narrowing the archwire groove. The tension spring will also apply a force against an installed archwire which will tend to rotate an individual tooth, if desirable. Hence, after the installation of the bracket and the archwire, a continuing force will be applied to the archwire from the stressing of the bracket which can result in major corrective forces: a tip force, a rotation force, a torque force, and an extrusion or intrusion force being applied to the tooth.

An object of the present invention is the provision of an orthodontic bracket assembly.

Another object of the present invention is the provision of an improved orthodontic bracket assembly.

Another object of the invention is the provision of an orthodontic bracket with built-in spring tension for applying orthodontic forces to a tooth.

Yet another object of the invention is the provision of a spring-stressed orthodontic bracket for applying orthodontic forces after installation thereof.

Other objects and many of the attendant advantages of the present invention will be readily appreciated as the same becomes better understood by reference to the following detailed description when considered in connection with the accompanying drawings in which like reference numerals designate like parts throughout the Figures thereof and wherein:

FIG. 3 is a perspective view of one jaw member of the embodiment of FIG. 2,

FIG. 4 is a bottom view in the direction of arrow 5 of FIG. 5.

FIG. 5 is an exploded view of the embodiment of FIG. 2;

DETAILED DESCRIPTION OF THE DRAWING

Figure 1:
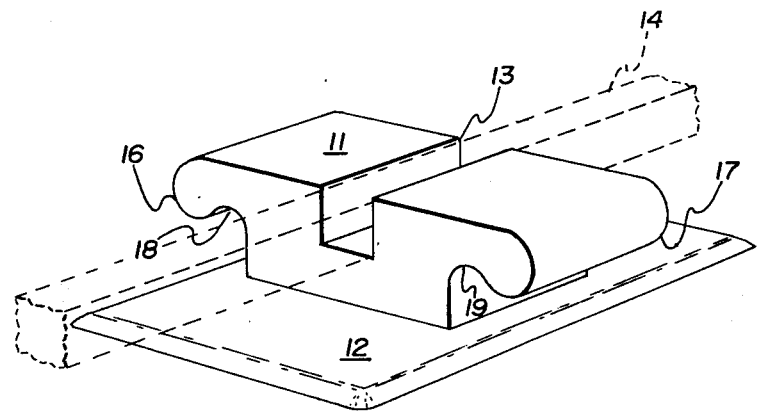
FIG. 1 is a perspective view of a typical prior art orthodontic bracket.

Referring to FIG. 1, an orthodontic bracket 11 has an archwire groove 13 for receiving an archwire 14 (in dotted lines) therein. Tie wings 16 and 17 define tie wing grooves 18 and 19, respectively.

Figure 2:
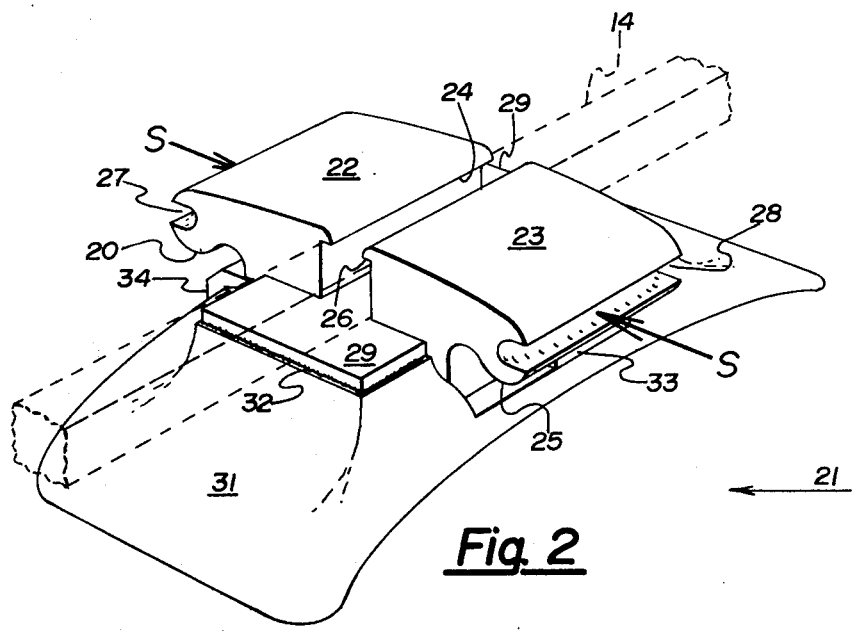
FIG. 2 is a perspective view of the preferred embodiment of the present invention.

Referring to FIG. 2, orthodontic bracket 21 has first and second single jaw members 22 and 23 defining a groove for the reception of archwire 14 (in dotted lines) therebetween. Single jaw members 22 and 23 each has a lip 24 and 26, respectively, for capturing archwire 14 therein. Single jaw members 22 and 23 have spring retention grooves 27 and 28, respectively. Retainer plate 29 has a central portion riding between jaw members 22 and 23 and is attached to base member 31 as by brazing. Arrows S—S indicate the forces exerted by a spring placed within grooves 27 and 28.

Referring to FIG. 3, single jaw member 22 is illustrated in perspective with its top surface terminating in an overhanging lip 24 on one edge and in the spring retaining groove 27 on another edge. Sliding tongue 33 extends from beneath the main portion of single jaw 22 to terminate at a beveled edge 30.

Referring to FIG. 4, the undersides of two mated single jaw members 22 and 23 are shown partially broken away. Here the edges of lips 24 and 26 are shown in the broken away section together with the edges of retaining grooves 27 and 28 in dotted lines. It is noted here that the corners of retaining grooves 27 and 28 have a radius for more efficient coupling to the retaining spring (FIG. 5). Elongated grooves 22A and 23A cooperate with limit pins (FIG. 5) to limit the outward movement of the two single jaw members 22 and 23, as will be explained with reference to FIG. 5.

Referring to FIG. 5, an exploded view of the embodiment of FIG. 2 is shown with single jaw members 22 and 23 coupled together with their sliding tongue portions 33 and 34, respectively, abutting each other. Beveled portion 30 of single jaw member 23 enables a tie wire to be placed between sliding tongue 34 and the bottom curved surface 20 of single jaw member 22. A similar beveled surface 30 is on sliding tongue portion 33 of single jaw 22 as shown in FIG. 3. Overhanging lips 24 and 26 of single jaw members 22 and 23 serve to help capture an archwire (not shown) within the groove formed between the vertical surfaces of single jaw members 22 and 23. Base member 31 has plateau surfaces 36 and 37 which is a recessed surface 40 on which the sliding tongues 33 and 34 rest. Limit pins 38 and 39 extend upwardly from recessed surface 40 and ride in elongated recesses 22A and 23A (FIG. 4) of single jaw members 22 and 23, respectively. After single jaw members 22 and 23 are placed on recess surface 40 of base 31, they are separated horziontally, as illustrated, and retainer plate 29 is placed between the two single jaw members. Sections 29B and 29C are then fixedly attached to surfaces 36 and 37, respectively, of base 31 as by brazing, with section 29A disposed between the two single jaw members 22 and 23. This will serve to capture single jaw members 22 and 23 within recess 40 and will limit the movement of single jaw members 22 and 23 to the abutment of section 29A. Spring member 41 has sections 41A and 41B which ride in spring retaining grooves 27 and 28, respectively, forcing single jaw members 22 and 23 together. Sections 41C and 41D serve to rotate the tooth when required as will be discussed with reference to FIG. 6. Sections 41E, 41F, 41G and 41H serve to allow a tie wire to be placed underneath the cleat portions of the bracket which would be beneath retaining grooves 27 and 28 and above sliding tongues 30 and 33.

Figure 6:
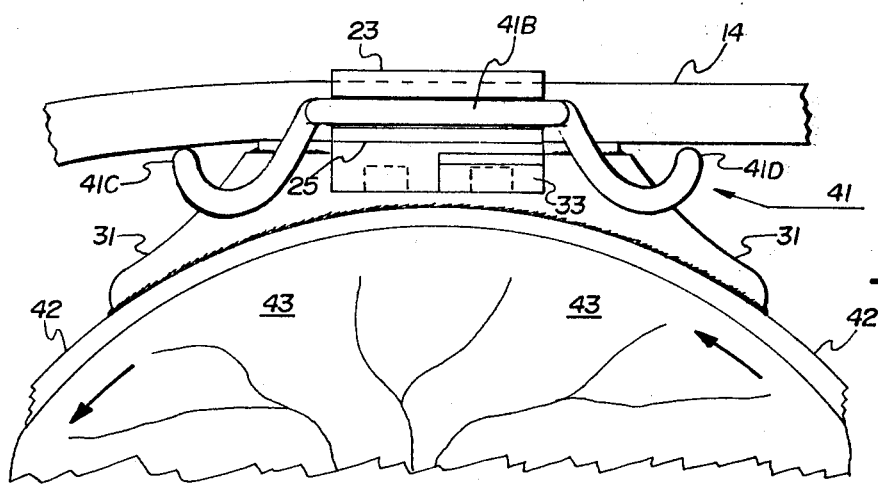
FIG. 6 is a top view of the embodiment of FIG. 7 in situ.

Referring to FIG. 6, spring 41 is shown with section 41B within spring retaining groove of single jaw member 23. Here archwire 14 is shown within the space between two single jaw members, one of which cannot be seen. Sections 41C and 41D of spring 41 are normally free of contact from archwire 14 if a tooth to which the bracket is attached does not require rotation. Here, the bracket base 31 is brazed, soldered or welded to toothband 42 around tooth 43 (or can be bonded directly to tooth 43) and tooth 43 requires rotation in the direction of the arrows. This distortion places section 41C in spring stress against archwire 14 forcing the rotation in the direction indicated by the arrows. If the tooth were to be rotated in an opposite direction, section 41D would be contacting archwire 14.

Figure 7:
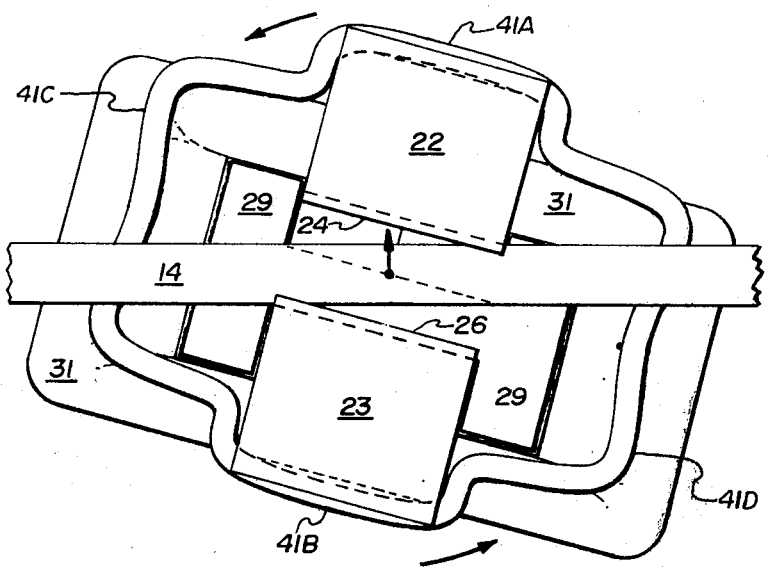
FIG. 7 is a side elevational view of the embodiment of FIG. 2 during treatment.

Referring to FIG. 7, the bracket assembly is shown as it would appear on a tooth requiring a tipping and an intrusion force vector (assuming an upper tooth). Here single jaw member 22 has been forced upwardly by the placement of archwire 14 between the end surfaces of single jaw members 22 and 23 with single jaw member 23 abutting both one surface of retainer plate 29 and archwire 14. Hence, the force vectors applied to a tooth would be in the upward direction, as indicated by the arrow, and a rotation of the bracket, and hence, a tipping of the tooth in a counterclockwise direction. It can be seen that sections 41A and 41B of spring 41 have been distended to a stretched tensioned position.

Figure 8:
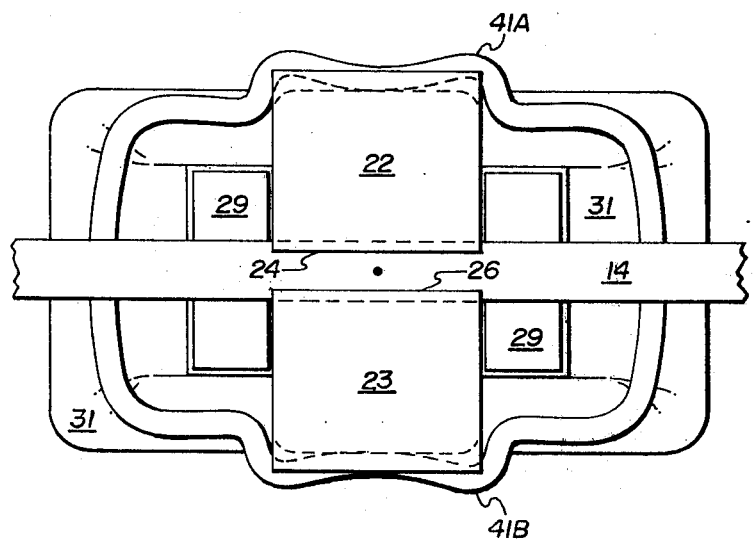
FIG. 8 is a side elevational view of the embodiment of FIG. 2 after treatment.

Referring to FIG. 8, the assembly of FIG. 7 is shown after the rotation and intrusion movements have taken place, i.e., the single jaw members 22 and 23 are now symmetrically disposed on base 31, the tooth having been intruded and tipped counterclockwise. Here it is noted that sections 41A and 41B of spring 41 are returned to their quiescent state as being slightly concave. It is further pointed out here that spring sections 41A and 41B in FIG. 5 would be concave, but in the interest of clarity and simplicity, they have been shown as being linear.

It can be seen that through the utilization of a spring stressed orthodontic bracket of the present invention, continual forces will be present on a given tooth which will be exerted by the bracket assembly itself and not through the distortion of the archwire. It is emphasized that these forces applied to a tooth will be relatively constant throughout the orthodontic treatment, resulting in a more rapid and consistent movement of teeth during treatment.

It should be understood, of course, that the foregoing invention relates to only a preferred embodiment of the invention, and that it is intended to cover all changes and modifications of the example of the invention herein chosen, for the purposes of the disclosure, which do not constitute departures from the spirit and scope of the invention.

The invention claimed is:

1. A spring-stressed orthodontic bracket comprising:
   first and second jaw members;
   a base member, said first and second jaw members being coupled to and carried by said base member, at least one of said first and second jaw members being in slidable relationship with the other of said first and second jaw members;
   biasing means coupled to at least one of said first and second jaw members and operable for biasing said first and second jaw members toward each other for defining at least one arch wire groove;
   at least one limit pin extending outwardly from said base member; and
   at least one elongated groove in said at least one of said first and second jaw members geometrically disposed for receiving said at least one pin base member for limiting relative movement thereof.

2. The spring-stressed orthodontic bracket of claim 1 wherein said biasing means comprises:
   a tension spring coupled to said first and second jaw members.

3. The spring-stressed orthodontic bracket of claim 2 wherein:
   said tension spring has at least one segment dimensioned for contact with an installed arch wire and operable for exerting a rotational force on said first and second jaw members.

4. A spring-stressed orthodontic bracket comprising:
   first and second jaw members;
   a base member, said first and second jaw members being coupled to and carried by said base member, said first and second jaw members each being in slidable relationship with the other;
   biasing means coupled to said first and second jaw members and operable for biasing said first and second jaw members toward each other for defining an arch wire groove;
   first and second limit pins extending outwardly from said base member; and
   first and second elongated grooves in said first and second jaw members, respectively, said first and second elongated grooves geometrically disposed for receiving said first and second limit pins, respectively, in said base member for limiting movement thereof.

5. The spring-stressed orthodontic bracket of claim 4 wherein said biasing means comprises:
   a tension spring in contact with the outer edges of said first and second jaw members.

6. The spring-stressed orthodontic bracket of claim 5 wherein:
   said tension spring has at least one segment dimensioned for contact with an installed arch wire and operable for exerting a rotational force on said first and second jaw members.

* * * * *